US00PP35428P2

(12) United States Plant Patent
Roe

(10) Patent No.: US PP35,428 P2
(45) Date of Patent: Oct. 17, 2023

(54) ***PHILODENDRON* RED MOON PLANT NAMED 'FIRE MOON'**

(50) Latin Name: *Araceae Philodendron*
Varietal Denomination: Fire Moon

(71) Applicant: Robert Roe, Umatilla, FL (US)

(72) Inventor: Robert Roe, Umatilla, FL (US)

( * ) Notice: Subject to any disclaimer, the term of this patent is extended or adjusted under 35 U.S.C. 154(b) by 0 days.

(21) Appl. No.: 17/864,996

(22) Filed: Jul. 14, 2022

(51) Int. Cl.
*A01H 5/12* (2018.01)
*A01H 6/10* (2018.01)

(52) U.S. Cl.
USPC ..... Plt./381
CPC ..... *A01H 6/10* (2018.05)

(58) Field of Classification Search
USPC ..... Plt./381
CPC ..... A01H 6/00; A01H 6/10; A01H 5/12
See application file for complete search history.

(56) References Cited

PUBLICATIONS

Wikipedia, List of *Philodendron* Species, https://en.wikipedia.org/wiki/List_of_Philodendron_species, downloaded Sep. 29, 2022.*
8 Facts about the *Philodendron* Red Moon—Grower Today, https://www.growertoday.com/philodendron-red-moon/, downloaded Sep. 29, 2022.*

* cited by examiner

*Primary Examiner* — Keith O. Robinson
(74) *Attorney, Agent, or Firm* — Andrew S. Rapacke

(57) ABSTRACT

A new and distinct cultivar of *Philodendron* Red Moon named 'Fire Moon' particularly characterized by its distinctive leaf appearance; large plant size; mostly open and outwardly spreading fuller plant habit; vigor and slow growth rate; less-freely branching; flat leaves; and long and wide petioles with long petiole sheaths.

4 Drawing Sheets

BACKGROUND

The present invention relates to a new and distinct cultivar of *Philodendron* Red Moon plant, botanically known as Araceae *Philodendron* Red Moon, and hereinafter referred to by the cultivar name 'Fire Moon.'

The new *Philodendron* Red Moon is a product of an accidental breeding by the Inventor in Umatilla, Fla.

The new *Philodendron* Red Moon originated from an accidental breeding made by the Inventor in May 2021, of an unidentified selection of the Araceae *Philodendron* Red Moon. The cultivar 'Fire Moon' was discovered and selected by the Inventor on May 2021, as a fully grown plant in a 8" Growers Pot container within the progeny of the self-pollination in a controlled environment in Umatilla, Fla.

Compared to plants of the parent selection, plants of the new *Philodendron* Red Moon are larger, branch earlier, are less freely branching, and have a fuller plant habit and longer petioles.

Asexual propagation of the new *Philodendron* Red Moon by cuttings at Umatilla, Fla. has shown that the unique features of this new *Philodendron* Red Moon plant are stable and reproduced true to type in successive generations.

SUMMARY OF THE INVENTION

The new *Philodendron* Red Moon has not been observed under all possible environmental conditions. The phenotype may vary somewhat with variations in environment such as temperature, light intensity, fertilizer rate, and/or irrigation amount and frequency without any variance in genotype.

The following traits have been repeatedly observed and are determined to be the unique characteristics of 'Fire Moon.' These characteristics in combination distinguish 'Fire Moon' as a new and distinct cultivar.

1. Plants of the new *Philodendron* Red Moon are self-heading, not vining, and are self-supporting.
2. Plants of the new *Philodendron* Red Moon are relatively large in size with a mostly upright, somewhat outwardly spreading and open plant habit.
3. Plants of the new *Philodendron* Red Moon are vigorous and have a slow growth rate.
4. Plants of the new *Philodendron* Red Moon branch slowly and are early branching.
5. Plants of the new *Philodendron* Red Moon have large, thick, smooth, and flat leaves with one-half light red and one-half light yellow-green.
6. Plants of the new *Philodendron* Red Moon have relatively long petioles and long, green, pink, and red-colored petiole sheaths.

Plants of the new *Philodendron* Red Moon can be compared to plants of the commercial *Philodendron* cultivars 'Little Hope' (U.S. Plant Pat. No. 26,282) and 'Prince of Orange' (U.S. Plant Pat. No. 06,797). However, in side-by-side comparisons conducted in Umatilla, Fla., plants of the new *Philodendron* Red Moon differ from plants of the cultivar 'Little Hope' and 'Prince of Orange' in the following characteristics:

1. Plants of the new *Philodendron* Red Moon are larger and are more outwardly spreading and open than plants of the cultivar 'Little Hope' and 'Prince of Orange.'
2. Plants of the new *Philodendron* Red Moon are less vigorous, form branches earlier and are less freely branching than plants of the cultivar 'Little Hope' and 'Prince of Orange.'

3. Leaves of plants of the new *Philodendron* Red Moon are thicker, more ovate in shape with truncate bases, and have more numerous primary veins than leaves of plants of the cultivar 'Little Hope' and 'Prince of Orange.'
4. Leaf color of plants of the new *Philodendron* Red Moon is darker green and there is a more striking contrast between the mid rib and the surrounding leaf tissue compared to leaves of plants of the cultivar 'Little Hope' and 'Prince of Orange.'
5. Plants of the new *Philodendron* Red Moon have longer and wider petioles than plants of the cultivar 'Little Hope' and 'Prince of Orange.' In addition, the shape of the petiole also differs longer, wider, and with green, red, and pink markings.
6. Leaf petiole sheaths of plants of the new *Philodendron* Red Moon are greener and darker in color than leaf petiole sheaths of plants of the cultivar 'Little Hope' and 'Prince of Orange.' Plants of the new *Philodendron* Red Moon can also be compared to plants of the commercial *Philodendron* Red Moon cultivar "'Little Hope' and 'Prince of Orange.' However, in side-by-side comparisons conducted in Umatilla, Fla., plants of the new *Philodendron* Red Moon differ from plants of the cultivar 'Little Hope' and 'Prince of Orange' in the following characteristics:

1. Plants of the new *Philodendron* Red Moon are larger and are more outwardly spreading and open than plants of the cultivar 'Little Hope' and 'Prince of Orange.'
2. Plants of the new *Philodendron* Red Moon are less vigorous, form branches earlier and are less freely branching than plants of the cultivar 'Little Hope' and 'Prince of Orange.'
3. Leaves of plants of the new *Philodendron* Red Moon are thicker, more ovate in shape with truncate bases and have more numerous primary veins than leaves of plants of the cultivar 'Little Hope' and 'Prince of Orange.'
4. Leaf color of plants of the new *Philodendron* Red Moon is half yellow-green, half red whereas leaf color of plants of the cultivar 'Little Hope' and 'Prince of Orange' is green. Additionally, there is a more striking contrast between the midrib and the surrounding leaf tissue on plants of the new *Philodendron* Red Moon compared to leaves of plants of the cultivar 'Little Hope' and 'Prince of Orange.'
5. Plants of the new *Philodendron* Red Moon have longer and wider petioles than plants of the cultivar 'Little Hope' and 'Prince of Orange.' In addition the shape of the petiole also differs.
6. Leaf petiole sheaths of plants of the new *Philodendron* Red Moon are greener and darker in color than leaf petiole sheaths of plants of the cultivar 'Little Hope' and 'Prince of Orange.'
7. Plants of the new *Philodendron* Red Moon flower later than plants of the cultivar 'Little Hope' and 'Prince of Orange.'

BRIEF DESCRIPTION OF THE PHOTOGRAPHS

The accompanying color photographs illustrate the overall appearance of the new *Philodendron* Red Moon 'Fire Moon,' showing the colors as true as it is reasonably possible to obtain in color reproductions of this type.

The photographs on sheets one through four comprise top perspective views of a typical plant of 'Fire Moon' including immature leaves in a (size, e.g. 15 cm) container.

DETAILED BOTANICAL DESCRIPTION

The following observations, measurements, and comparisons describe plants grown in Umatilla, Fla., under a polycarbonate-covered greenhouse and conditions which closely approximate those used in general, standard commercial horticultural practice. Plants were grown in fertilized soil under day temperatures ranging from 25 to 32 C and night temperatures ranging from 22 to 27 C. Light level ranged from 800 to 2,000 footcandles.

Plants used for this description were asexually reproduced by taking cuttings (twigs), rooted and planted into fertilized soil in 15-cm containers. Information was collected for this description and the cultivar comparisons in May, 2022, when the plants were about 2 months old from taking cuttings (twigs). Numerical measurements represent averages from typical plants. Environmental conditions were tropical, humid, and required less water than typical *Philodendron* Red Moon.

In the following description, color references are made to The Royal Horticultural Society Colour Chart except where general terms of ordinary dictionary significance are used.

Botanical classification: Araceae *Philodendron* Red Moon cultivar 'Fire Moon.'

Parentage: Self-pollination of an unidentified selection of Araceae *Philodendron* Red Moon.

*Propagation: type.*—By taking cuttings (twigs).

*Time to initiate roots.*—Summer: About 21 days at about 25 to 30° C. Winter: About 28 days at about 22 to 27° C.

*Time to develop* (*time to produce a rooted liner*).—Summer: About 10 to 12 weeks at about 25 to 30° C. Winter: About 13 to 14 weeks at about 22 to 27 C.

*Rooting habit.*—Strong root system. Main roots thick; abundant lateral roots. Thick short aerial roots are occasionally observed.

Plant description:

*Growth habit.*—Self-heading, not vining, and self-supporting. Mostly upright, but outwardly spreading, open, freely branching, Somewhat asymmetrical; mature plants, more rounded in overall shape. Appropriate for 15 to 25-cm containers.

*Plant size.*—Height, Soil Surface to top of leaf canopy: About 50.7 cm. Width: About 99.2 cm.

*Plant vigor.*—Vigorous, slow growth rate.

*Crop time.*—About 48 to 52 weeks are required to produce a 40 to 50-cm tall plant in a 15-cm container from a 1 to 2-cm taken cutting (twigs).

*Foliage description.*—Shape of leaves on young plants: Between elliptic and ovate; apex, acuminate with some acute tendencies, base, obtuse; margin, entire. Shape of leaves on older plants: Ovate, apex, acuminate with Some acute tendencies, base, truncate; margin, entire. Length, mature leaves: About 36.7 cm. Width, mature leaves: About 18.8 cm. Length to width ratio, mature leaves: About 1.95 to 1. Aspect: Almost flat; Slightly concave at the petiole attachment. Texture: Thick, leathery, smooth. Surface: Glossy; young leaves very glossy. Color: Young, upper surface: At unrolling: Slightly darker than 144A. Once unrolled: Much darker than 144A.

Young, lower Surface: 144A. Mature, upper surface: Darker than 147A. About 1mm wide band along margin, lighter green, 144A. Mature, lower surface: Darker and Slightly greener than 144A, with subsequent development, leaf becomes slightly darker and greener than 147B. Venation, upper Surface of mature leaves: Midrib adjacent to petiole, 144B to 146B to 146C with short darker green striae; distal, darker green, 147A. Primary veins are slightly lighter green than surrounding leaf tissue. Venation, lower surface of mature leaves: midrib and primary veins, mostly 146C. Petiole aspect: Erect to semi erect. Petiole shape: Rounded lower Surface; upper Surface Slightly concave. Petiole length, primary shot: About 43.4cm. Petiole diameter, just below leaf blade: About 10.3 mm. Petiole sheath length: About 21.2 cm. Petiole color, young leaves: 144A to 146C with short darker green striae. Petiole color, upper Surface of mature leaves: Adjacent to leaf blade, close to 146A to 146B with Some 144A, proximally darker to 146A to 147B; slightly lighter near base. Short darker green Striae. Petiole color, lower Surface of mature leaves: Adjacent to leaf blade, close to 146B to 146D and 14.4A to 144B; proximally darker, close to 146A, base, close to 144A. Short darker green striae. Petiole sheath:144B and 144D with short darker green striae, Some grayed orange, close to 166C to 166D, present at proximal end near edges, more noticeable at distal end.

*Inflorescence.*—Typical of *Philodendron* Red Moon, no commercial significance. Plants typically form inflorescences about 18 to 23 months after planting of a twig taken from cutting. Description of inflorescences taken from plants grown for about 2.5 years after planting a twig taken from cutting.

*Arrangement.*—Spathes with spadices with one to three inflorescences in each floral sympodium. Each developing inflorescence enclosed by two sheaths, which deteriorate before spathe opens. Spathes erect, situated near shoot base on short, thick, usually bent peduncles. Spathes typically tightly tolled around spadices, Spathes typically open for about one day. When spathes are open, the spadix is fully exposed, leaning forward beyond spathe margins, at about 50 to penduncle axis.

*Fragrance.*—Weak, Similar to other *Philodendrons*, but weaker.

*Peduncle.*—Length: About 7.3 cm. Diameter: About 1.5 cm. Color: 144B or between 144B and 144C.

*Spathe.*—Shape: Boat-shaped; longitudinal section elliptic; apex between acuminate and cuspidate; base, obtuse; margin, entire and usually rolled back especially distally. Length: About 18.3 cm. Width: About 7.6 cm. Length to width ratio: About 2.4 to 1. Depth: About 4.8 cm. Texture: Very thick, fleshy, not glossy. Color: Open, front surface: Between 47A and 47B around spadix base, distally and toward margin, much lighter, 48D to 49D to close to 159C near apex with some scattered light pink. Some yellow green, 144B, on midrib and along margins near apex. Open, rear surface: Most of the central Zone of proximal half is an uneven color, varying between different combinations of 146C, 146D, 144A, 144B and 144C. Color becomes lighter and more yellow towards margins, near margins, between145Cand 145D and translucent. In the distal half, there is a band along midrib between 144B, and 146C and 146D. Spathe color on either side of this band is variable, but much lighter and more yellow, most areas more yellow than 145C and more green than 150C. Often there is a wide, almost whitish, translucent band on one side near the margin.

*Spadix.*—Shape: Cylindrical, Strongly tapering towards acute apex. Female Zone, Situated at the base, shorter than the male Zone and Separated by an intermediate Sterile Zone. Sterile and male Zones not clearly distinguished when Spathe is open. Spadices typically sessile. Length: About 17.1 cm; female Zone, about 4.8 cm; Sterile and male Zones combined, about 12.6 cm. Diameter: Female Zone, about 1.9 cm; sterile and male zones, about 1.8 cm proximally. Color: Female Zone, between 145C and 145D; sterile and male zones, slightly darker than 159C. Pollen: Cream in color. Dehiscence about one to three days after spathe closes.

*Seed production.*—Seed production has not been observed. Typically, spathes and spadices gradually deteriorate after spathe closure.

Disease tolerance: Resistance to pathogens common to *Philodendron* Red Moon has not been observed.

What is claimed is:

1. A new and distinct cultivar of *Philodendron* Red Moon plant named 'Fire Moon', as illustrated and described.

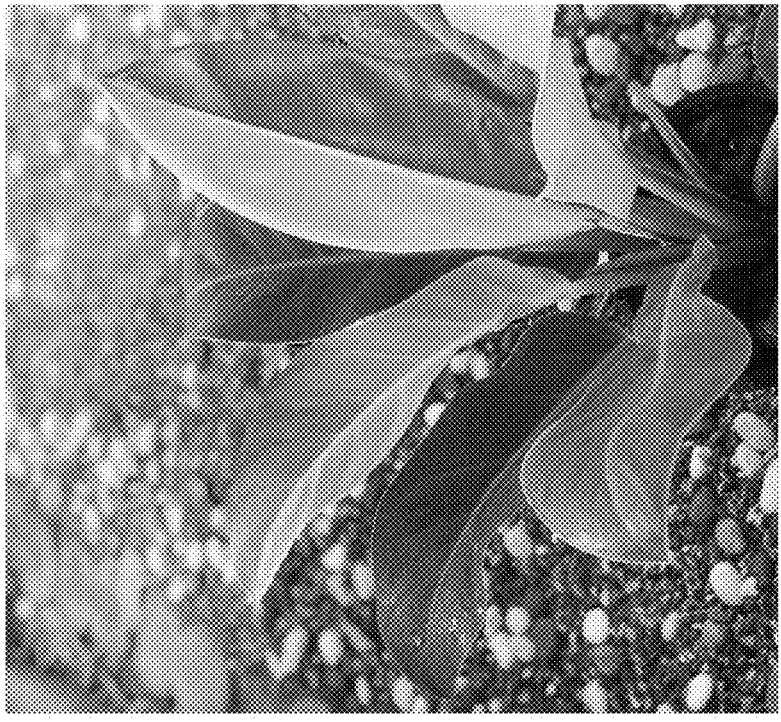

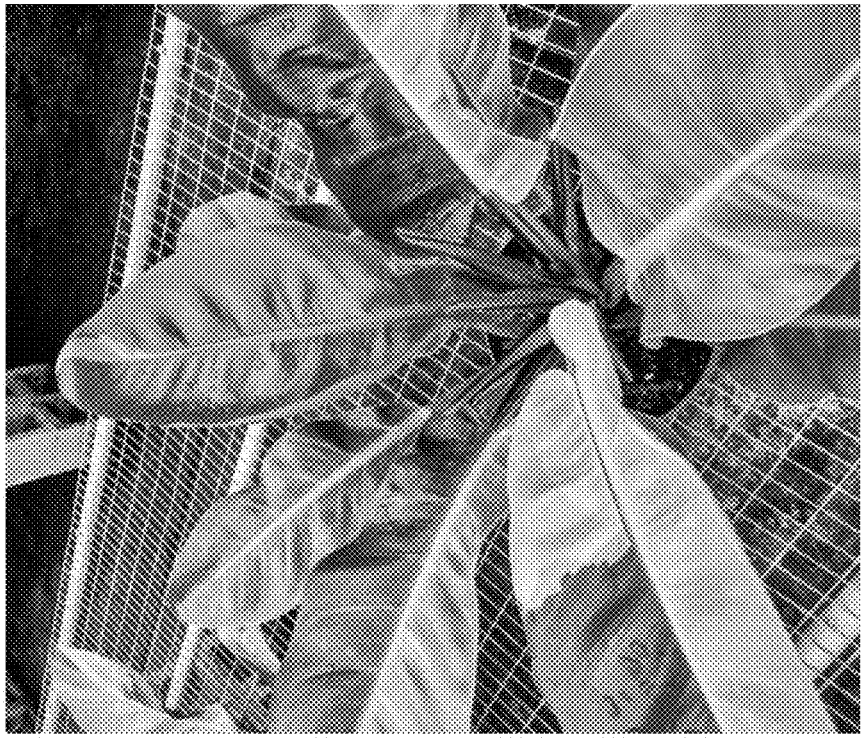

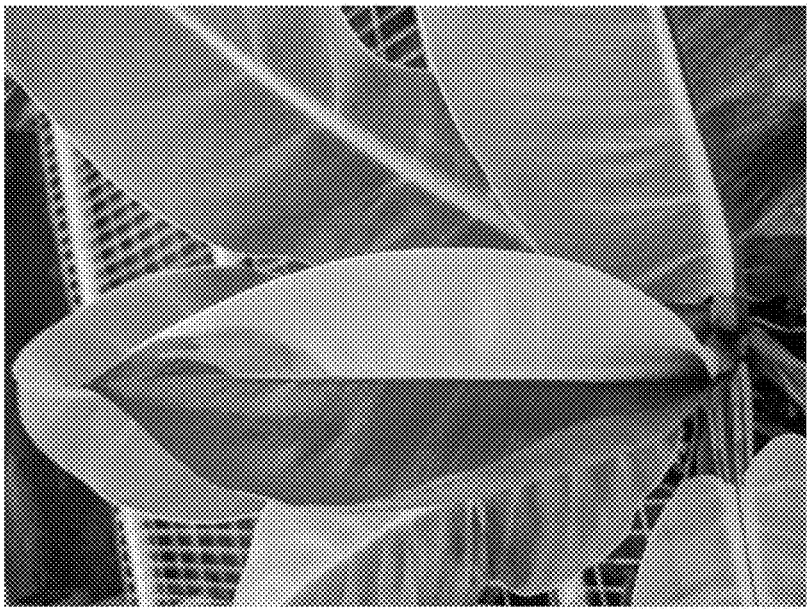

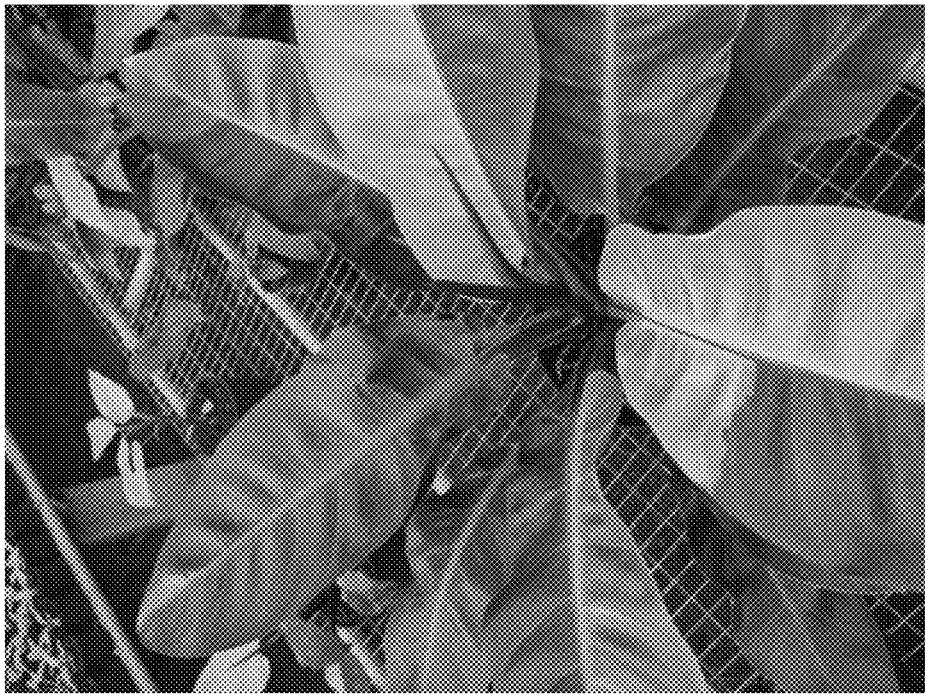

* * * * *